(12) United States Patent
Kinast et al.

(10) Patent No.: US 11,045,349 B2
(45) Date of Patent: Jun. 29, 2021

(54) DEVICE FOR MEASURING AND IMPROVING ADHERENCE OF EYE DROPS

(71) Applicant: Universal Adherence LLC, Portland, OR (US)

(72) Inventors: Robert Michael Kinast, Portland, OR (US); Steven Larry Mansberger, Portland, OR (US)

(73) Assignee: Universal Adherence LLC, Portland, OR (US)

( * ) Notice: Subject to any disclaimer, the term of this patent is extended or adjusted under 35 U.S.C. 154(b) by 885 days.

(21) Appl. No.: 15/547,058

(22) PCT Filed: Jan. 29, 2016

(86) PCT No.: PCT/US2016/015600
§ 371 (c)(1),
(2) Date: Jul. 27, 2017

(87) PCT Pub. No.: WO2016/123456
PCT Pub. Date: Aug. 4, 2016

(65) Prior Publication Data
US 2018/0008459 A1    Jan. 11, 2018

Related U.S. Application Data

(60) Provisional application No. 62/110,498, filed on Jan. 31, 2015.

(51) Int. Cl.
*A61F 9/00* (2006.01)
*A61M 5/168* (2006.01)
*B65D 47/06* (2006.01)

(52) U.S. Cl.
CPC .............. *A61F 9/0008* (2013.01); *A61F 9/00* (2013.01); *A61M 5/1689* (2013.01); *B65D 47/06* (2013.01)

(58) Field of Classification Search
CPC ......... A61F 9/00; A61M 5/1689; B65D 47/06
USPC ........................................................ 604/298
See application file for complete search history.

(56) References Cited

U.S. PATENT DOCUMENTS

| 5,009,338 A | 4/1991 | Barker |
| 5,012,496 A | 4/1991 | Weinreb et al. |
| 5,014,798 A | 5/1991 | Glynn |
| 5,417,349 A | 5/1995 | Stull |

(Continued)

FOREIGN PATENT DOCUMENTS

WO    WO2014106759 A1    7/2014

OTHER PUBLICATIONS

PCT Patent Application No. PCT/US16/15600; International Search Report and Written Opinion dated Apr. 14, 2016.

(Continued)

*Primary Examiner* — Andrew J Mensh
(74) *Attorney, Agent, or Firm* — Schwabe, Williamson & Wyatt, P.C.

(57) ABSTRACT

An adherence device 100, including an attachable component to secure to an eye drop bottle cap and a monitoring component 110. The monitoring component 110 includes a sensor 170 to detect each eye drop administration. The attachable component may be a "universal cap" capable of securing onto any eye drop bottle cap while still permitted normal FDA-approved water-tight closure. The cap is capable of being removed and transferred to a different eye drop bottle for reuse.

17 Claims, 7 Drawing Sheets

(56) References Cited

U.S. PATENT DOCUMENTS

| | | | |
|---|---|---|---|
| 5,694,882 | A | 12/1997 | Marshall |
| 5,860,387 | A | 1/1999 | Giveen |
| 6,016,764 | A | 1/2000 | Giveen |
| 6,877,626 | B2 | 4/2005 | Sherrod |
| 7,081,807 | B2 | 7/2006 | Lai |
| 8,026,796 | B2 | 9/2011 | Kiran |
| 8,269,613 | B2 | 9/2012 | Lazar |
| 8,279,076 | B2 | 10/2012 | Johnson |
| 8,319,613 | B2 | 11/2012 | Lazar |
| 8,998,861 | B2 | 4/2015 | Fateh |
| 9,361,780 | B2 * | 6/2016 | Burke, Jr. ............... G16H 20/13 |
| 2002/0104848 | A1 | 8/2002 | Burrows et al. |
| 2003/0089733 | A1 * | 5/2003 | Cain ..................... A61J 7/0481 |
| | | | 222/30 |
| 2004/0039355 | A1 | 2/2004 | Gonzalez et al. |
| 2009/0051560 | A1 | 2/2009 | Manning et al. |
| 2010/0142330 | A1 * | 6/2010 | Reygaert ............... A61J 1/1418 |
| | | | 368/10 |
| 2010/0270257 | A1 | 10/2010 | Wachman et al. |
| 2011/0119090 | A1 * | 5/2011 | Lazar ....................... A61J 1/14 |
| | | | 705/3 |
| 2012/0150132 | A1 | 6/2012 | Cress |
| 2014/0228783 | A1 | 8/2014 | Kraft |
| 2015/0351960 | A1 * | 12/2015 | Cooper ................ A61F 9/0026 |
| | | | 604/521 |

OTHER PUBLICATIONS

Friedman et al.; "The TRAVATAN Dosing Aid Accurately Records When Drops are Taken"; Brief Reports; vol. 143, No. 4; p. 699-701.

Hermann et al.; "Microprocessor controlled compliance monitor for eye drop medication", Br. J. Ophthalmol. 2006; 90; p. 830-832; 1996.

Kass et al.; "Compliance with Topical Pilocarpine Treatment"; American Journal of Ophthalmology; vol. 101, No. 5; p. 515-523; May 1986.

* cited by examiner

DEVICE FOR MEASURING AND IMPROVING ADHERENCE OF EYE DROPS

CROSS REFERENCE TO RELATED APPLICATIONS

The present application is a national phase entry under 35 U.S.C. § 371 of International Application No. PCT/US2016/015600, filed Jan. 29, 2016, entitled "DEVICE FOR MEASURING AND IMPROVING ADHERENCE OF EYE DROPS," which designated, among the various States, the United States of America, and which claims priority to U.S. Provisional Patent Application No. 62/110,498 filed Jan. 31, 2015, both of which are hereby incorporated by reference.

TECHNICAL FIELD

The present disclosure relates generally to medical devices for monitoring medication adherence, and more particularly to devices for measuring and improving the adherence of eye drop medications.

BACKGROUND

Glaucoma is a chronic ocular disease in which the optic nerve is progressively damaged due to elevated intraocular pressure. Physicians routinely prescribe glaucoma eye drops to lower intraocular pressure and thus prevent the disease from worsening. However, glaucoma eye drops must be taken every day to be effective. Thus, adherence to ocular medications is critical to preventing visual impairment from glaucoma.

Glaucoma is the second leading cause of blindness, affecting over 48 million people in the U.S. and worldwide. In the U.S. alone, glaucoma care costs more than $8.1 billion. Poor adherence to treatment (defined as using less than 75% of prescribed eye drop doses) is prevalent; approximately 50% of glaucoma patients do not adhere to therapy. Poor adherence creates greater visual loss and a higher risk of blindness, and non-adherence is a leading cause of blindness in those with glaucoma. Currently, researchers and eye care providers do not have a suitable device to measure and improve the eye drop taking behavior of glaucoma patients.

DETAILED DESCRIPTION OF DISCLOSED EMBODIMENTS

Figure 1A:
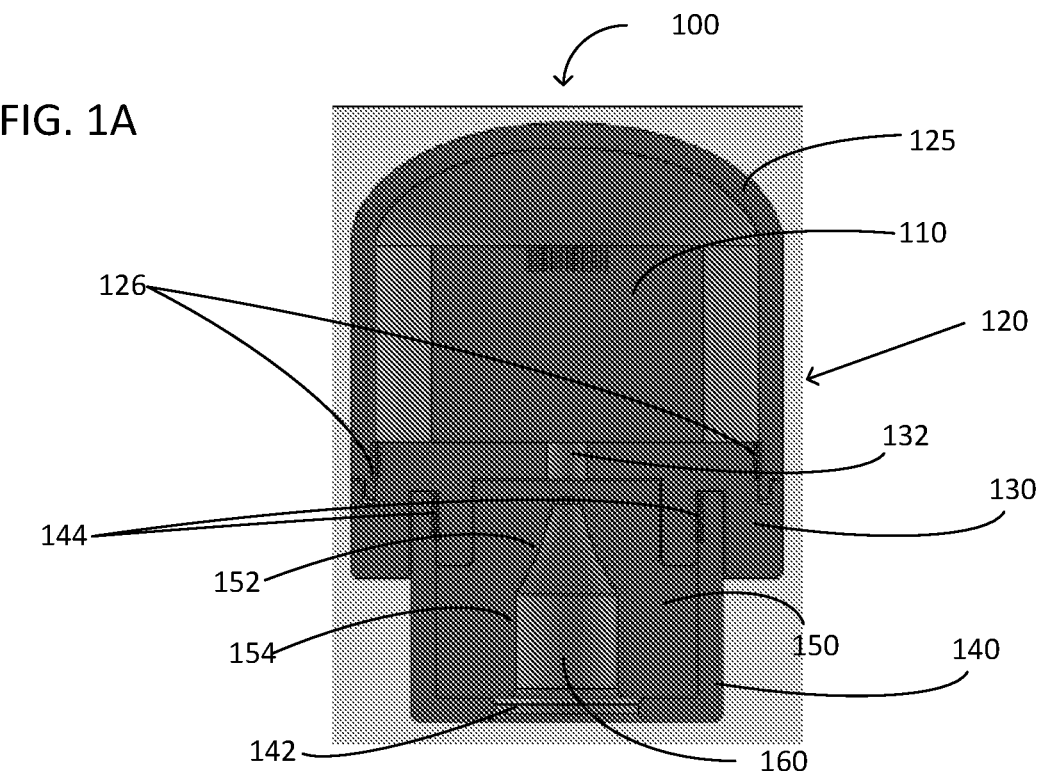
FIG. 1A shows a schematic vertical mid-cut view of an example of an adherence device, in accordance with various embodiments.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical contact with each other. "Coupled" may mean that two or more elements are in direct physical contact, or electronic contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Eye drops present unique problems for measuring adherence when compared to devices to measure the usage of oral pills, such as tablets for systemic hypertension. For example, the Federal Drug Administration (FDA) approves an eye drop medication based not only on the efficacy of the medication, but also on the specific characteristics of the container holding the medication. Thus, the FDA will not allow the use of bottles that have not been approved for that specific medication because of concerns regarding sterility, drop quantity, and drop volume. Therefore, any dose monitor for eye drops must be able to utilize the water-tight bottle that the FDA has approved for that medication. Currently, the bottle shapes and sizes vary widely for the more than 25 different types of ocular hypotensive medications available for treating glaucoma.

At least in part because of these issues, researchers and eye care providers have had difficulty developing a suitable device to measure the drop-taking behavior of glaucoma patients. Currently, an existing eye drop monitor is available for only one brand of eye drop (TRAVOPROST®). However, this monitor requires pressing a mechanical lever to record administering an eye drop, so the monitor is prone to overestimate adherence when placed in a bag or pocket. Furthermore, this monitor is cumbersome, inaccurate, and only fits one eye drop bottle.

Another design for measuring adherence is called the MEMSCap™. This device employs an electronic bottle and cap that measures pill counts, and can also accommodate some small eye drop bottles. This "bottle within a bottle" mechanism for eye drop compliance requires that the patient remove the MEMSCap™, remove the eye drop bottle, remove the eye drop bottle's cap, dispense the eye drop, replace the bottle's cap, replace the bottle in the MEMSCap™ container, and replace the MEMSCap™. This cumbersome process deviates from the usual process of administering eye drops, thereby limiting the objectivity of the device for measuring true drop-taking behaviors. The GlowCaps® pillbox and e-Pill Multi-Alarm Time-Cap are additional examples of the "bottle within a bottle" mechanism, and they share the same disadvantages, including poor accuracy, as patients often forget to place the eye drops bottle back in the pill bottle.

Accordingly, there is a need for an adherence device that allows for the accurate measurement and improvement of adherence for multiple different bottle shapes. This device must permit water-tight closure of each FDA-approved bottle. The device may be detachable so that it may be transferred and reused on refills of subsequent eye drop bottles. An adherence device that addresses all of the above-mentioned drawbacks would provide more accurate measurement and improvement of eye drop adherence leading to preserved vision in millions of individuals and, potentially, save billions of dollars.

Disclosed herein in various embodiments are adherence devices for monitoring and/or recording adherence to eye drop medication usage that is particularly suited to monitoring a subject's adherence to glaucoma treatment using eye drops. The disclosed device has been designed to "universally" fit and removably attach securely to various bottle types, solving both the problem of variable bottle type and reusability. In addition, the device has been designed to passively (for example without additional user input beyond removing and/or replacing the top) and accurately measure when an eye drop is administered, by simply measuring when the eye drop bottle top is removed from the eye drop bottle and/or replaced on the bottle (for example to avoid spillage or evaporation).

In various embodiments, information may be collected about adherence, such as the date and time that the eye drop bottle was opened and/or closed. This information may be stored on the device and/or communicated to a secondary device, such as a computer and/or hand held device (such as a tablet, a phone, or the like), for example wirelessly. In some embodiments, the data may be distributed through a network, for example to contacts (e.g., patients, family, physicians, and/or pharmacy) or social media, for example to provide motivational feedback. In various embodiments, adherence data may be wirelessly transferred with Bluetooth, Wi-Fi, and/or other local or non-local communication. The data may be shared with contacts (e.g., patients, friends, family, physicians, and/or pharmacy) and may provide instant adherence feedback. In some embodiments, adherence data may be compared with peers to provide additional social motivation. In some embodiments, the device may include programmable alerts, for example to alert the patient when an eye drop is due. Such alerts may be from the device itself, for example as a chime or flashing light, or through a secondary device, such as a hand held device or computer, for example as a text message or other notification.

In various embodiments, the adherence device may include an attachable component, for example an eye drop bottle cap grip, and a monitoring component. In various embodiments, the monitoring component may include a sensor for sensing when the eye drop bottle cap is removed from and/or replaced onto the bottle. In some embodiments, information about the time and date when the eye drop bottle cap is removed and/or replaced may be collected, for example by electronics connected to the sensor, and may be stored, for example in memory within the device, and/or transmitted from the device to a secondary device, such as a hand held device (for example a phone, a PDA, or specific monitoring device), or a computer, such as a desktop or laptop computer, where the information can be stored for later use, viewing, analysis, etc.

As disclosed herein, the monitoring component may include a sensor that is capable of determining when an eye drop bottle cap is removed and/or replaced on an eye drop bottle. In various embodiments, the monitoring component may include a sensor, such as a gyroscopic sensor (for example sensing twisting of the eye drop bottle top), an electromagnetic sensor, a pressure sensor, a mechanical sensor, a light/laser sensor, or a combination thereof. In certain embodiments, the sensor may be a magnetic sensor, and it may detect a change in the position of a ferromagnetic material or magnet, such as a ferromagnetic material or magnet coupled to or incorporated into the eye drop bottle, and the device may be rotated with respect to the ferromagnetic material or magnet when the eye drop bottle cap is twisted or otherwise removed and/or replaced. In some embodiments, the ferromagnetic material or magnet may take the form of a magnetic tape, which may be placed on the bottle prior to use.

In other embodiments, a light or laser sensor may be used to detect changes in a reflective material disposed on the eye drop bottle as the device is rotated with the eye drop bottle cap. Thus, in some embodiments, a reflective or light-emitting material may be placed on the eye drop bottle. In other embodiments, a mechanical and/or pressure sensor may likewise be used, for example to physically detect the presence of the cap on the bottle. Typically, the sensor and/or accompanying electronics may be programmed to limit false positive and false negative eye drop administration readings.

In various embodiments, the monitoring component may include a circuit coupled to associated electronics, for example for detecting, storing, and transmitting adherence information. In embodiments, the monitoring component may include a microprocessor coupled to the circuit. In various embodiments, the monitoring component may include a real-time clock, for example to date and/or time stamp adherence information. In some embodiments, the monitoring component may include a transmitter and/or a receiver, such as a Wi-Fi and/or Bluetooth transmitter and/or receiver coupled to the circuit. In some examples, the Wi-Fi and/or Bluetooth transmitter and/or receiver may be coupled to an antenna.

In some embodiments, the monitoring component may include a power source coupled to the circuit, such as a battery, to power the device. In various embodiments, the monitoring component may include an alert, such as a visual or audio alert, coupled to the circuit, for example to alert the user that they are due for their next dose of eye drops. In some embodiments, the circuit may include a storage medium, such as memory, for storing information about the removal and/or replacement of the cap from the bottle. In some embodiments, the information may be transmitted passively, that is without user input. In some embodiments, the information may be transmitted through an action of use, for example by tripping a switch or button that has been coupled to the circuit.

In various embodiments, circuits may be in the form or circuit board, either designed or adapted for use in the monitoring component. Such circuit boards are available through various vendors, for example the TinyDuino circuits available from TinyCircuits (world wide web at tiny-circuits.com).

As disclosed herein, in various embodiments, the adherence monitoring device may include an attachable component, which, in some embodiments, may be mechanically coupled to the monitoring component. In some embodiments, the attachable component may be a "universal eye drop cap on a cap" that is capable of attaching and detaching from an eye drop bottle cap design. In various embodiments, the device may be configured to secure onto multiple different eye drop bottle caps, so when turning the device, the bottle cap would simultaneous turn in its naturally designed threads, preserving the FDA-approved water tight fit. In other embodiments, the attachable component may secure at the base of the bottle or clasp securely around the neck or body of the bottle. In some embodiments, the attachable component may be a universal cap capable of attaching onto any or many eye drop bottle cap designs. In some embodiments, the attachable component may include a resilient material to fit in a "hand-in-glove" approach so the attachable component plugs firmly onto the bottle cap. Alternatively, in various embodiments, the device may attach to the bottle cap using mechanical tightening, such as with gears and clasps.

In the attachable component, the attachable component may include an eye drop bottle cap grip, which may effectively hold the eye drop bottle cap securely, such that the cap rotates when the device is rotated. In various embodiments, the eye drop bottle cap grip may include an inner grip section that fits over an eye drop bottle cap, for example an inner grip section that includes an inner surface that follows the general contours of an eye drop bottle cap.

By way of example, many eye drop bottle caps are shaped with a substantially vertical wall section (there is some degree of taper typically associated), sometimes fluted, that is used to turn the cap, and a bottle nosed section that tapers from the vertical walled section upward to an end. Typically, this tapered section follows generally the contour of the eye drop dispenser it covers. Thus, in various embodiments, the eye drop bottle cap grip may likewise include a vertical walled portion to contact the vertical wall portion on the cap and a tapered portion to contact the tapered portion of the cap. In some embodiments, the inner grip section may include a vertically convex section and a substantially straight vertical section, which may slightly taper as it extends upward. In certain embodiments, the vertically convex section may taper from a larger diameter to a smaller diameter, and the larger diameter may be substantially the same diameter as the top end of the substantially straight vertical section. In alternate embodiments, the tapered portion may be excluded. In certain embodiments, the inner grip section has a substantial smooth gripping surface. In certain embodiments, the inner grip section may include at least a portion with a variable gripping surface, for example ribs and/or fingers. In some embodiments the eye drop bottle cap grip may include a lip at the bottom that fits over the bottom of the cap to help secure the cap in place.

In various embodiments, the inner grip section may be fashioned from a pliable and/or resilient material that may conform to the shape of the eye dropper bottle cap. Moldable elastomeric polymeric materials are particularly suited for this purpose. In some embodiments, the inner grip section may include a polymer. In certain embodiments, the polymer may be a silicone polymer.

In certain embodiments, the device may include a housing, for example to house the monitoring component, or portions thereof, and/or the attachable component, such as the eye drop bottle cap grip. In certain embodiments, the housing may include a hard shell covering one or more of the eye drop bottle grip and the monitoring component, although it is understood that portions of the monitoring component, such as the sensor may be exposed. In an alternate embodiment, the housing may be contiguous with the eye drop bottle grip, for example made from the same material. In certain embodiments, the housing may be composed of plastic or a similar durable and water-resistant material.

FIG. 1A is a schematic drawing showing an embodiment of an adherence device 100 in accordance with various embodiments. In the illustrated embodiment, adherence device 100 includes monitoring component 110, housing 120, and eye drop bottle cap grip 150. In various embodiments, monitoring component 110 may include a circuit and at least one sensor for sensing removal of the eye drop bottle cap, and associated electronics, such as a processor, memory, a battery, a transmitter (such as a WiFi or Bluetooth transmitter), and/or receiver. In the illustrated embodiment, housing 120 is a hard casing composed of three parts, top 125, base 130, and bottom 140. In the illustrated embodiment, top 125 is coupled, in some cases reversibly, to base 130. In the illustrated embodiment, top 125 is reversibly coupled to base 130 through threads 126. The reversible coupling of top 125 and base 130 allows for the top to be removed, for example to access and/or service monitoring component 110, for example to replace the battery. Also shown is aperture 132 in base 130, which may be included to allow wires to pass through to connect to a sensor and/or transmission button (not shown). Bottom 140 includes aperture 142, which fits over the top of an eye drop bottle top. In the illustrated embodiment, bottom 140 is reversibly coupled to base 130 with threads 144. In the illustrated embodiment, eye drop bottle top grip 150 includes inner surfaces 152, 154, which enclose cap volume 160. Cap volume 160 is generally shaped to follow the contours of an eye drop bottle cap, and is sized appropriately to fit a vast array of such tops from various vendors.

Figure 1B:
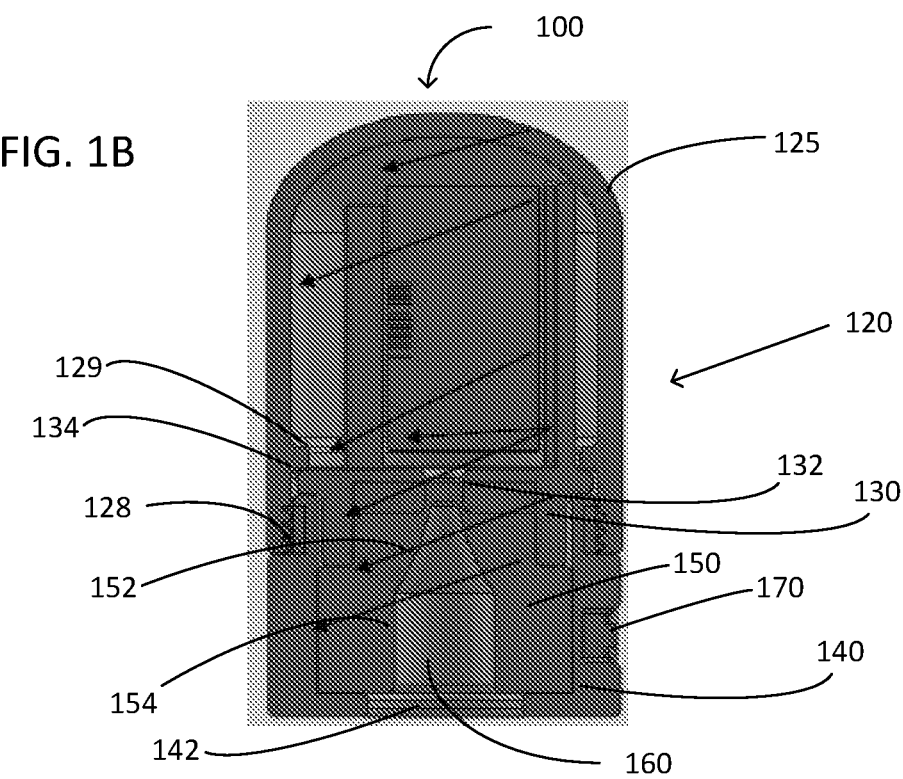
FIG. 1B shows a schematic vertical mid-cut view of an example of an adherence device, in accordance with various embodiments.

FIG. 1B is a schematic drawing showing an embodiment of an adherence device 100, in accordance with various embodiments. In the illustrated embodiment, adherence device 100 includes monitoring component 110, housing 120, and eye drop bottle cap grip 150. In various embodiments, monitoring component 110 may include a circuit and at least one sensor for sensing removal of the eye drop bottle cap, and associated electronics, such as a processor, memory, a battery, a transmitter (such as a WiFi or Bluetooth transmitter), and/or receiver. In the illustrated embodiment, housing 120 is a hard casing composed of three parts, top 125, base 130, and bottom 140. In the illustrated embodiment, top 125 is coupled, in some cases reversibly, to bottom 140, rather than base 130, as in the embodiment shown in FIG. 1A. In the illustrated embodiment, top 125 is reversibly coupled to bottom 140 through threads 128 and base 130 is held in place by inner flanges 129, 134. In various embodiments, the reversible coupling of top 125 and bottom 140 may allow for the top to be removed, for example to access and/or service monitoring component 110, for example to replace the battery. Also shown is aperture 132 in base 130, which allow wires to pass through to connect to a sensor and or transmission button 170. Bottom 140 includes aperture 142, which fits over the top of an eye drop bottle top. Eye drop bottle top grip 150 includes inner surfaces 152, 154, which enclose cap volume 160. Cap volume 160 is generally shaped to follow the contours of an eye drop bottle cap, and is sized appropriately to fit a vast array of such tops from various vendors.

Figure 1C:
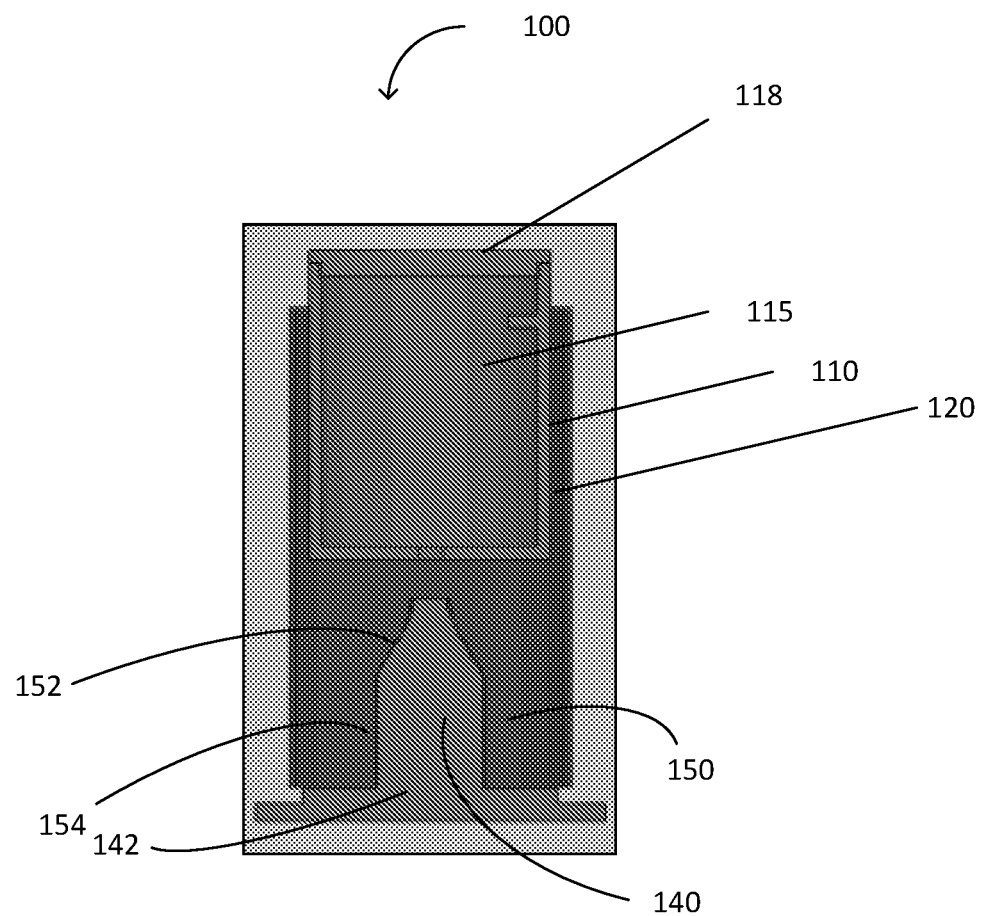
FIG. 1C shows a schematic vertical mid-cut view of an example of an adherence device, in accordance with various embodiments.

FIG. 1C is a schematic drawing showing an embodiment of an adherence device 100. In the illustrated embodiment, adherence device 100 includes monitoring component 110, housing 120, and eye drop bottle cap grip 150. In various embodiments, monitoring component 110 may include a circuit and at least one sensor for sensing removal of the eye drop bottle cap, and associated electronics, such as a processor, memory, a battery, a transmitter (such as a WiFi or Bluetooth transmitter), and/or receiver. In the embodiment shown, housing 120 is a soft casing that is contiguous with eye drop bottle cap grip 150. In the illustrated embodiment shown, monitoring component 110 is contained within compartment 115, and may be accessible through door 118, for example to access and/or service the monitoring component 110, for example to replace the battery. Bottom 140 includes aperture 142 which fits over the top of an eye drop bottle top. Eye drop bottle top grip 150 includes inner surfaces 152, 154, which enclose cap volume 160. Cap volume 160 is generally shaped to follow the contours of an eye drop bottle cap, and is sized appropriately to fit a vast array of such tops from various vendors.

Figure 2A:
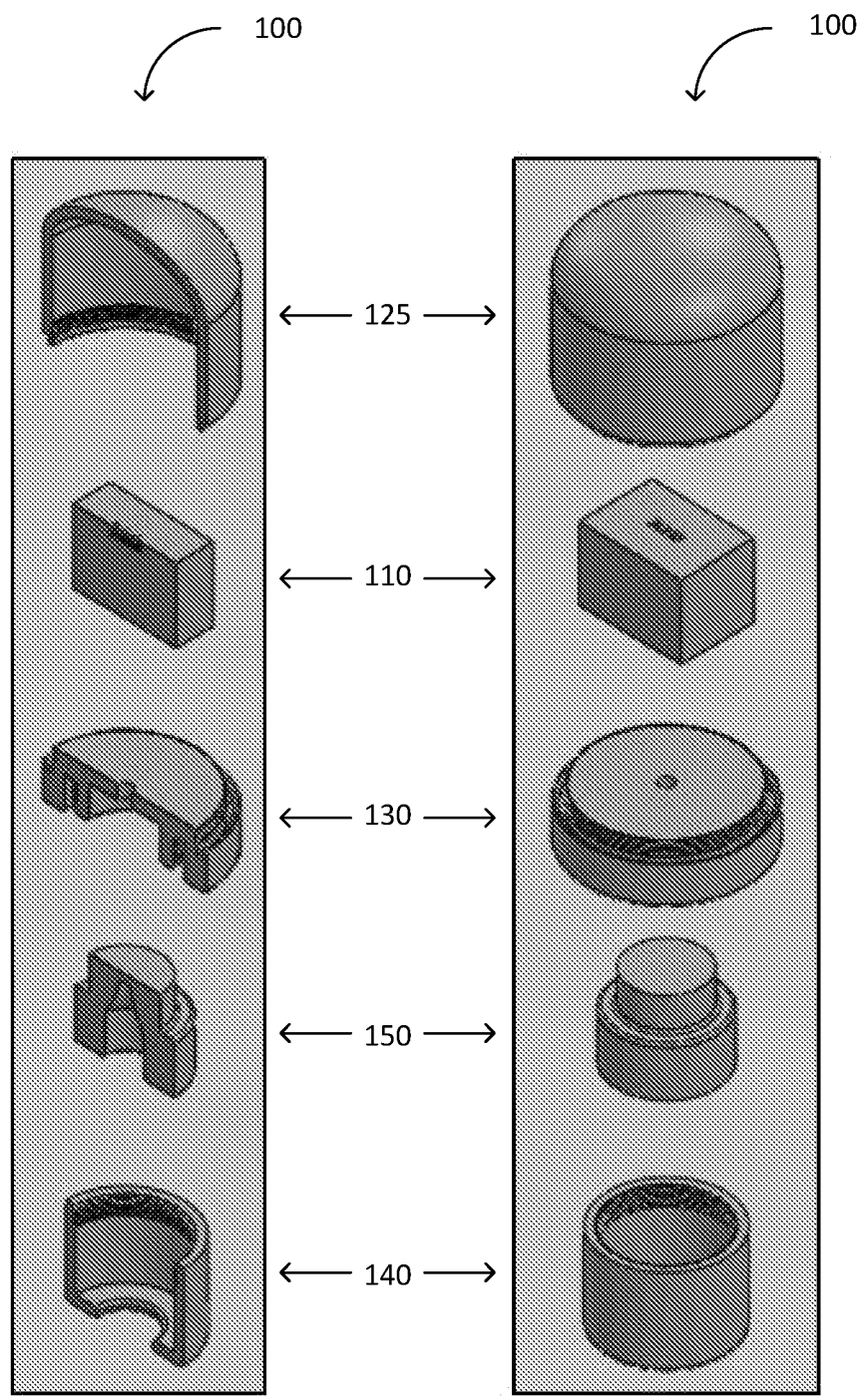
FIG. 2A shows a schematic exploded view of an example of an adherence device, in accordance with various embodiments.
Figure 2B:
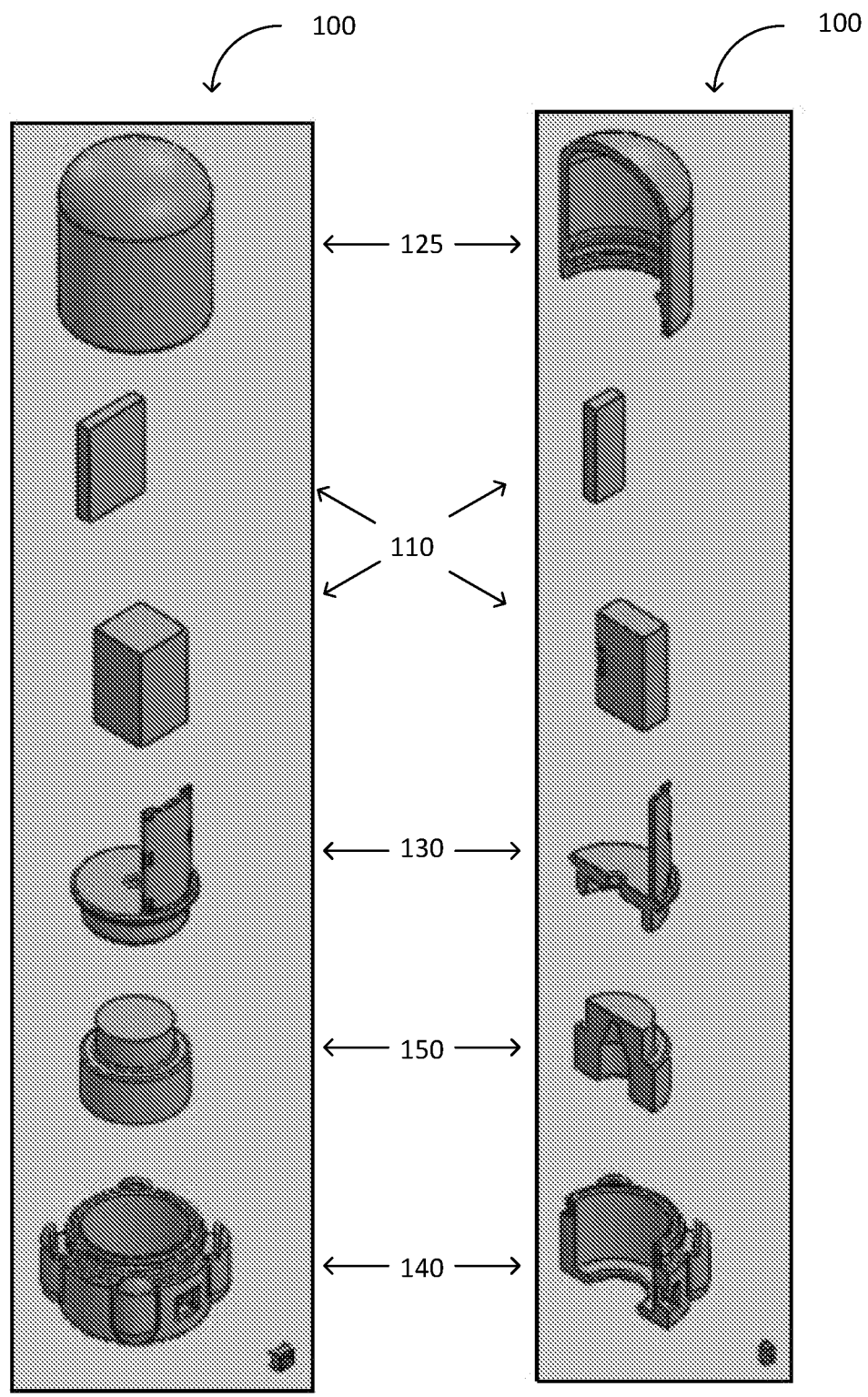
FIG. 2B shows a schematic exploded view of an example of an adherence device, in accordance with various embodiments.

FIGS. 2A and 2B illustrate exemplary exploded views of a disclosed adherence device, in accordance with various embodiments. In FIGS. 2A and 2B, adherence device 100 includes monitoring component 110, top 125, base 130, bottom 140, and eye drop bottle top grip 150.

Figure 3:
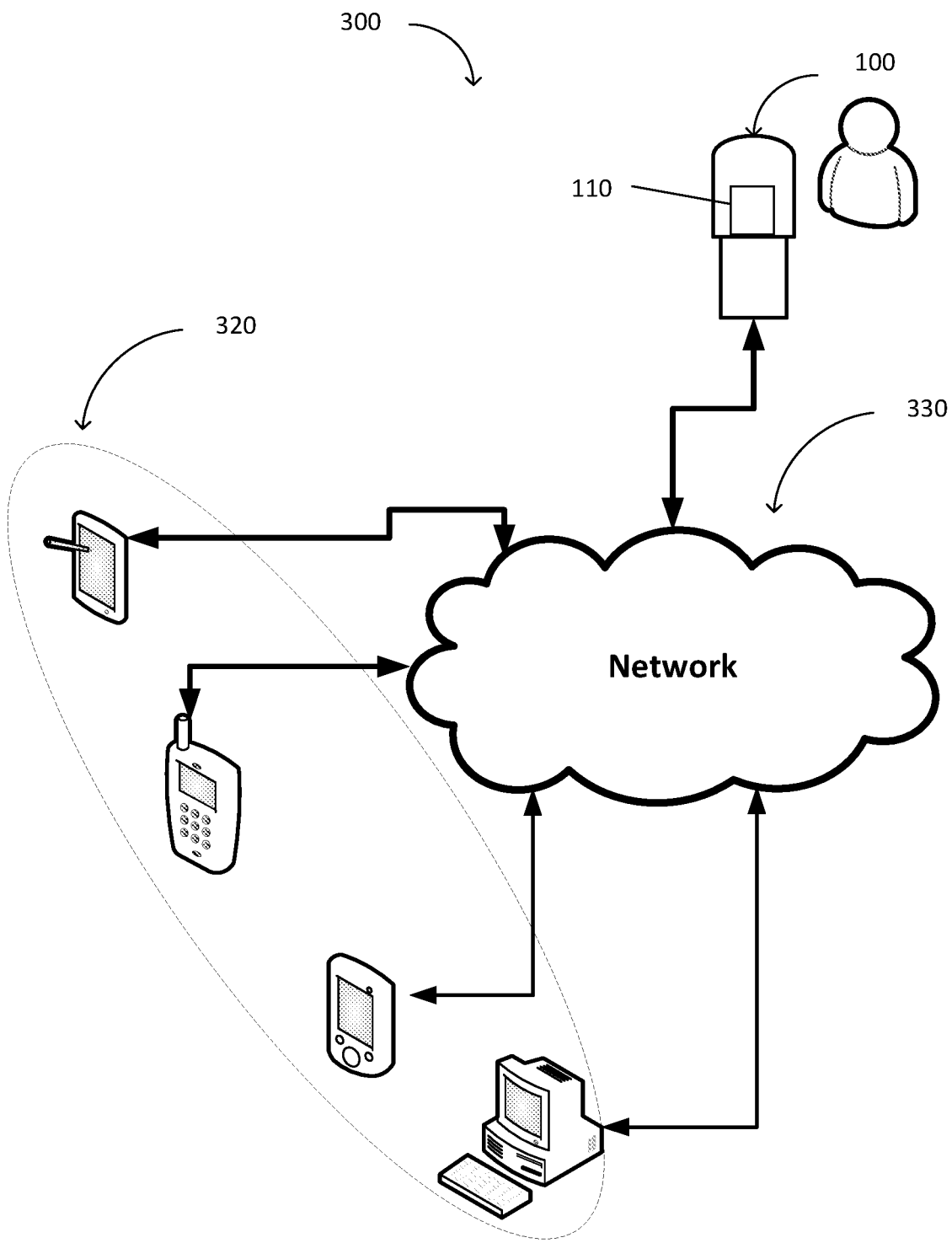
FIG. 3 is an example of a network for collecting and distributing adherence data, in accordance with various embodiments.

FIG. 3 is a block diagram depicting a system 300 for monitoring, collecting and distributing eye drop bottle use compliance information, in accordance with certain exemplary embodiments. As depicted in FIG. 3, the adherence monitoring device 100 distributes information to one or more networked devices 320 through one or more of network 330. Each network 330 includes a wired or wireless telecommunication means by which network systems (including systems adherence monitoring device 100 and networked devices 320) may communicate and exchange data. For example, each network 330 may be implemented as, or may be a part of, a storage area network (SAN), personal area network (PAN), a metropolitan area network (MAN), a local area network (LAN), a wide area network (WAN), a wireless local area network (WLAN), a virtual private network (VPN), an intranet, an Internet, a mobile telephone network, a card network, Bluetooth, near field communication network (NFC), any form of standardized radio frequency, or any combination thereof, or any other appropriate architecture or system that facilitates the communication of signals, data, and/or messages (generally referred to as data). Throughout this specification, it should be understood that the terms "data" and "information" are used interchangeably herein to refer to text, images, audio, video, or any other form of information that can exist in a computer-based environment.

In an example embodiment, each network system (including adherence monitoring device 100 and networked devices 320) includes a device having a communication component capable of transmitting and/or receiving data over the network 330. For example, each networked device (including adherence monitoring device 100 and networked devices 320) may comprise a server, personal computer, mobile device (for example, notebook computer, tablet computer, netbook computer, personal digital assistant (PDA), video game device, GPS locator device, cellular telephone, Smartphone, or other mobile device), a television with one or more processors embedded therein and/or coupled thereto, or other appropriate technology that includes or is coupled to a web browser or other application for communicating via the network 330.

Adherence monitoring device 100 includes at least one monitoring component 110 that is capable of detecting eye drop bottle cap removal and/or replacement initiated by a user. Monitoring component 110 is also capable of applying a date/time stamp to the opening/closing event and transmit this information to another device, such as one or more of networked devices 320, through network 330. In certain examples, monitoring component 110 is also capable of receiving information from one or more networked devices 320, through network 330, for example from a doctor or pharmacy reprograming networked devices 320, through network 330.

In an example embodiment, the monitoring component 110 of adherence device 100 has one or more processors embedded therein and/or coupled thereto, or other appropriate technology that can communicate via an electronic, magnetic, or radio frequency field between monitoring component 110 and another device. In an example embodiment, the monitoring component 110 has processing capabilities, such as storage capacity/memory and one or more applications (not illustrated) that can perform a particular function. In example embodiments monitoring component 110 includes a network controller, such as a Bluetooth controller. The controller may be capable of sending and receiving data, performing authentication and ciphering functions, and directing how monitoring component 110 will listen for and send transmissions from networked devices 320 or configure monitoring component 110 into various power-save modes, for example according to the Bluetooth-specified procedures. In another example embodiment, the controller is a Wi-Fi controller capable of performing similar functions.

In various embodiments, the monitoring component 110 may communicate with the networked devices 320 via an antenna. In an example embodiment, once the monitoring component is activated, for example by opening of the bottle, the controller is notified of the state of readiness of monitoring component for transmission. Alternatively, transmission may be triggered by activation of a switch, for example by the user to "download" one or multiple opening/closing events. In various embodiments, monitoring component 110 may output a radio signal through the antenna. On establishing a communication channel between monitoring component 110 and networked device 320, information may be transferred to the networked device.

An example monitoring component 110 may comprise a memory element (not shown), which can exist within a removable smart chip or a secure digital ("SD") card or which can be embedded within a fixed chip on monitoring component 110. In certain example embodiments, Subscriber Identity Identity Component ("SIM") cards may be used. In various embodiments, the memory element may allow a software application resident on the monitoring component 110.

In an example monitoring component 110 includes a processor. A processor can exist within a removable smart chip or can be embedded within a fixed chip on monitoring component 110. The application host processor may comprise applications (not shown) running thereon that perform the functionality described herein.

Figure 4:
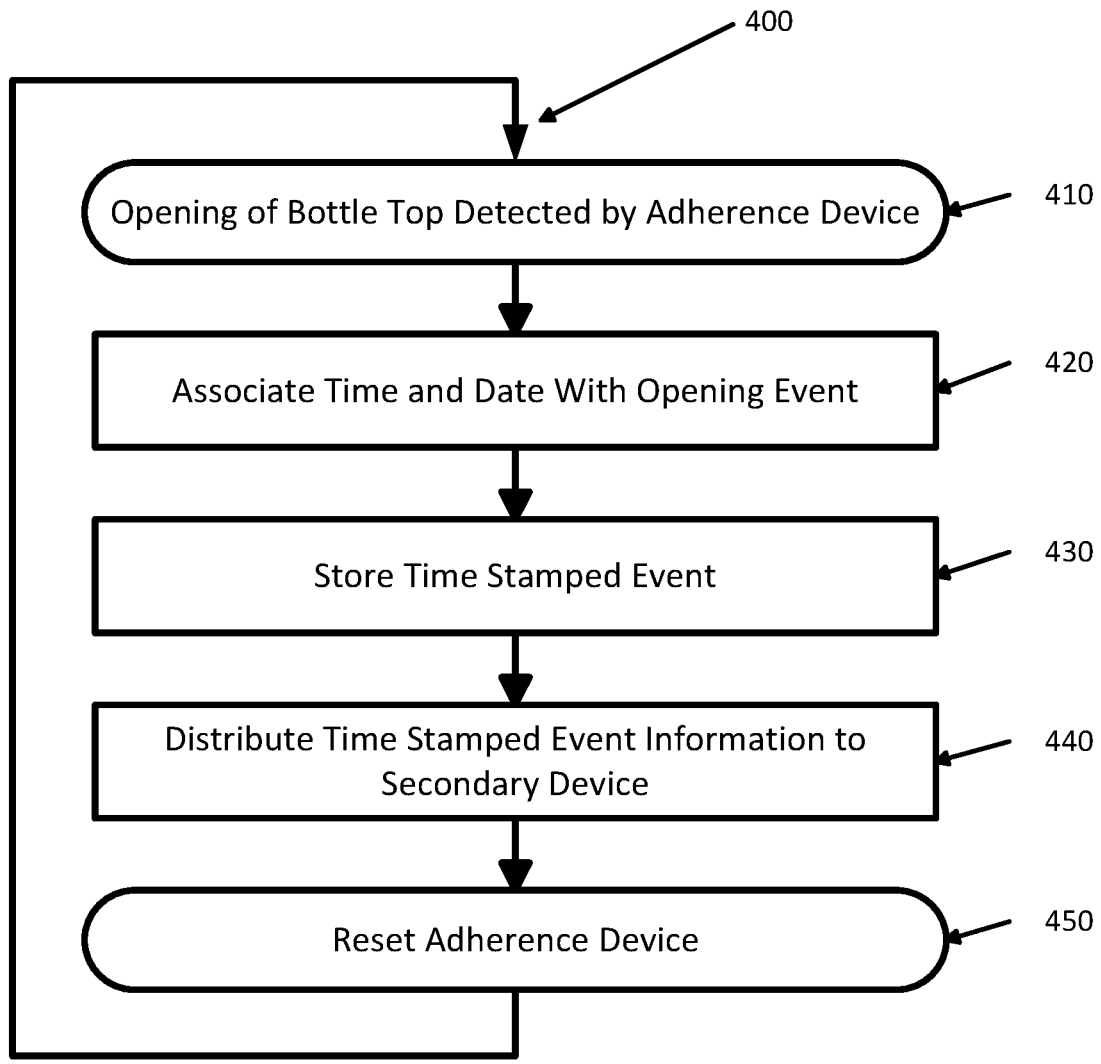
FIG. 4 is a block flow diagram depicting a method for collecting and distributing adherence data, in accordance with various embodiments.

FIG. 4 is a block flow diagram depicting an example method 400 for distributing adherence information from adherence device 100 and system 300, in accordance with example embodiments. In block 410, monitoring component 110 detects the opening of the eye drop bottle top which initiates subsequent activity. In block 420, the processor of monitoring component 110 associates a date and time with the event, for example using an internal clock to generate a date and time stamped event. In block 430 the date and time stamped event is saved into memory of monitoring component 110, for example for later retrieval. In block 440, the time and date stamped event information, or multiple stored information, is distributed to a secondary device, for example via WiFi or Bluetooth through an antenna of monitoring component 110. Once the information is date stamped and stored and/or distributed the monitoring component is reset for the next round of eye drop administration monitoring.

Figure 5:
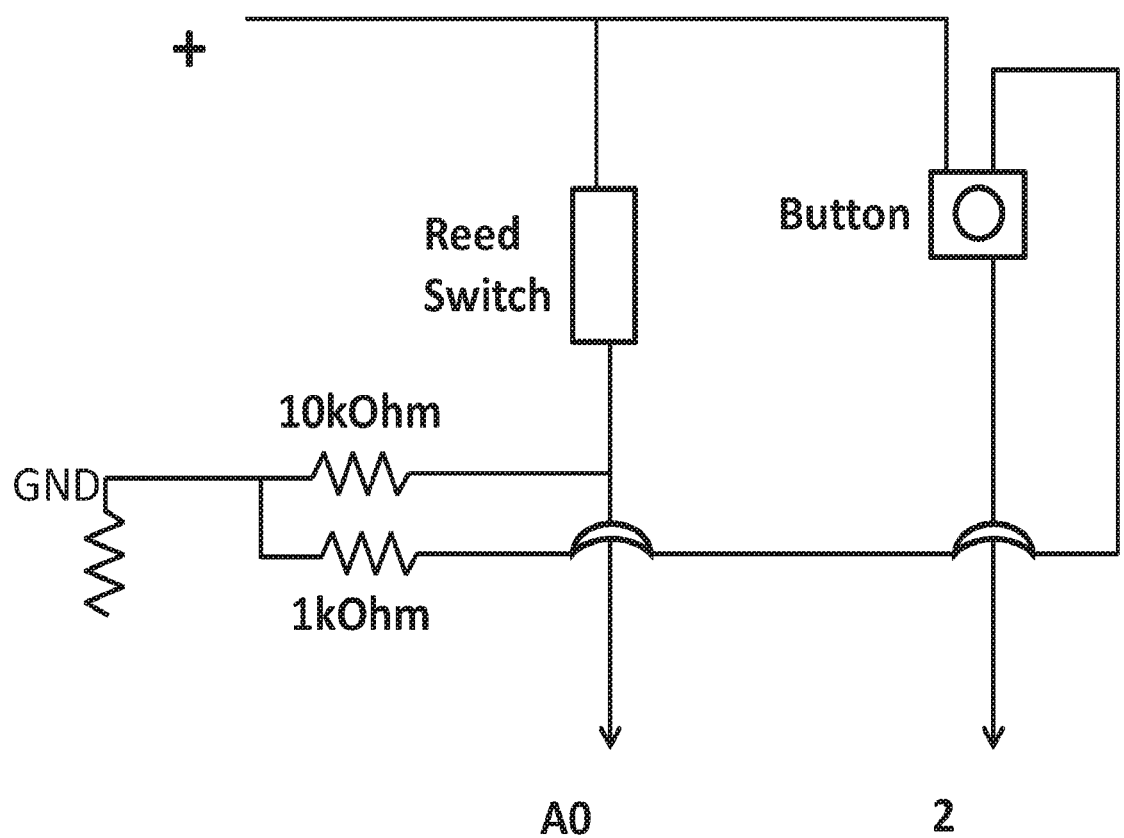
FIG. 5 shows a circuit diagram, in accordance with various embodiments.

FIG. 5 is a circuit diagram, in accordance with embodiments herein.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

We claim:

1. A device for measuring eye drop adherence, comprising:
    an outer shell that houses each of: an eye-drop bottle cap grip comprising an inner grip portion that fits over and removably couples to a bottle cap of any FDA-approved eye-drop bottle,
    a monitoring component comprising a sensor that senses removal of the bottle cap from the FDA-approved eye-drop bottle, a circuit coupled to the sensor to receive an indication of removal of the bottle cap, and a power source coupled to the circuit;
    wherein the inner grip portion comprises a variable gripping surface that includes a pliable material that conforms to a shape of the bottle cap; and
    wherein, when coupled to the bottle cap, the eye-drop bottle cap grip securely holds the bottle cap so that the bottle cap rotates with respect to the FDA-approved eye-drop bottle as the device is rotated, wherein no portion of the device contacts a medication contained within the FDA-approved eye-drop bottle nor a dispensing tip of the FDA-approved eye-drop bottle, and wherein the device permits watertight closure of the bottle cap to the FDA-approved eye-drop bottle.

2. The device of claim 1, wherein the device is reusable and couples to first and second bottle caps having different shapes and/or sizes.

3. The device of claim 1, wherein the sensor comprises a magnetic sensor; and
    wherein the magnetic sensor senses a magnetic material present on the FDA-approved eye-drop bottle.

4. The device of claim 3, wherein the magnetic material further comprises a magnetic tape placed on the FDA-approved eye-drop bottle.

5. The device of claim 1, wherein the monitoring component further comprises one or more of a storage medium for storing information about the removal of the bottle cap from the FDA-approved eye-drop bottle, and a transmitter for transmitting information about the removal of the bottle cap from the FDA-approved eye-drop bottle.

6. The device of claim 1, wherein the inner grip portion comprises an inner surface that follows general contours of the bottle cap.

7. The device of claim 1, wherein the variable gripping surface includes one or more of ribs and fingers.

8. The device of claim 1, wherein the pliable material comprises a polymer.

9. The device of claim 8, wherein the polymer comprises a silicone polymer or a moldable elastomeric polymer.

10. The device of claim 1, wherein the inner grip portion comprises a vertically convex section and a substantially straight vertical section.

11. The device of claim 10, wherein the vertically convex section tapers from a small diameter to a larger diameter and the larger diameter is substantially the same diameter as the substantially straight vertical section.

12. A system for measuring eye drop adherence, comprising:
    the device of claim 1, wherein the device further comprises a communication component for transmitting and/or receiving data to and/or from one or more networked devices.

13. The device of claim 1, wherein the sensor comprises a pressure sensor or a mechanical sensor capable of physically detecting a presence of the bottle cap of the FDA-approved eye-drop bottle.

14. The device of claim 1, wherein the sensor comprises an optical sensor capable of detecting changes in a reflective or light-emitting material disposed on the FDA-approved eye-drop bottle.

15. The device of claim 1, wherein the sensor comprises a gyroscopic sensor capable of sensing twisting of the device and/or bottle cap.

16. The device of claim 1, wherein the monitoring component further comprises a programmable alert to alert a user when an eye drop is due.

17. The device of claim 1, further comprising a switch or a button coupled to the circuit for initiating transmission of information pertaining to removal and/or replacement of the bottle cap from the FDA-approved eye-drop bottle.

* * * * *